(12) United States Patent
Lindel et al.

(10) Patent No.: US 11,312,696 B2
(45) Date of Patent: Apr. 26, 2022

(54) SYNTHESIS OF MORIN AND MORIN DERIVATIVES

(71) Applicant: ORSATEC GMBH, Bobingen (DE)

(72) Inventors: Thomas Lindel, Hannover (DE); Steffen Mende, Braunschweig (DE)

(73) Assignee: ORSATEC GMBH, Bobingen (DE)

( * ) Notice: Subject to any disclaimer, the term of this patent is extended or adjusted under 35 U.S.C. 154(b) by 0 days.

(21) Appl. No.: 16/765,594

(22) PCT Filed: Nov. 21, 2018

(86) PCT No.: PCT/EP2018/000521
§ 371 (c)(1),
(2) Date: May 20, 2020

(87) PCT Pub. No.: WO2019/101353
PCT Pub. Date: May 31, 2019

(65) Prior Publication Data
US 2020/0308131 A1    Oct. 1, 2020

(30) Foreign Application Priority Data
Nov. 21, 2017 (EP) .................................. 17202835

(51) Int. Cl.
*C07D 311/28*    (2006.01)
(52) U.S. Cl.
CPC .................. *C07D 311/28* (2013.01)
(58) Field of Classification Search
CPC ...................................... C07D 311/28
USPC ...................................... 549/400
See application file for complete search history.

(56) References Cited

FOREIGN PATENT DOCUMENTS

CN    1055985306    10/2016

OTHER PUBLICATIONS

International Search Report for PCT/EP2018/000521 dated Mar. 14, 2019.
Sheng, Xiao, et al., "The total synthesis of (±)-sanggenol F", Tetrahedron, vol. 73, No. 25, May 7, 2017, pp. 3485-3491.
Translation of International Search Report for PCT/EP2018/000521 dated Mar. 14, 2019.
Vyas, Bhawna, et al., "Pharmacophore and docking-based hierarchical virtual screening for the designing of aldose reductase inhibitors: synthesis and biological evaluation", Med. Chem. Res., vol. 25, Feb. 3, 2016, pp. 609-626.
Search Report for Singaporean Patent Application No. 11202004693P, dated Jun. 23, 2021.
Wang, et al., Journal of Chemical Research, 2015, 39, 300-302.

*Primary Examiner* — Taofiq A Solola
(74) *Attorney, Agent, or Firm* — Hueschen and Sage

(57) ABSTRACT

The invention relates to a method for directly producing morin derivatives and high-purity morin of formula (I). The invention also relates to morin derivatives and high-purity morin that can be obtained using the claimed method.

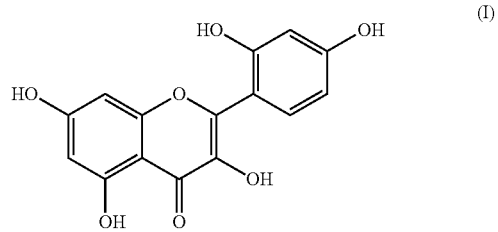

(I)

14 Claims, No Drawings

SYNTHESIS OF MORIN AND MORIN DERIVATIVES

The dyer's mulberry tree (*Maclura tinctoria* or *Orus tinctoria*) is a deciduous tree native to Central America, the Caribbean, East India, and tropical South America that can reach an average height of 20-30 m and a trunk thickness of 70-80 cm. The heartwood of the dyers mulberry tree is generally called yellow wood and had already been used to dye textiles in pre-Columbian times. The dyes in yellow wood are maclurin (also morintannic acid) and the pentahydroxy flavonol morin with the following formula I:

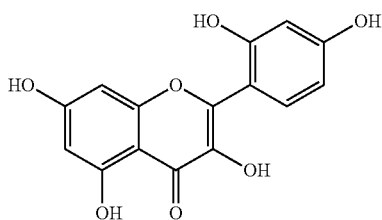

(I)

Morin (2,4-dihydroxyphenyl)-3,5,7-trihydroxy-4/7-chromen-4-one) belongs to the group of flavenols, a subgroup of flavonoids. The name of the mostly yellow plant dye is derived from the Latin name for yellow=*flavus*. Morin has five hydroxy groups and three cyclic systems. The basic skeleton of flavonols with numbering of the skeletal atoms, together with the structure-similar aurones and the open-chain chalcones, can be gathered from Fig. 1.

Morin has antioxidant properties, is anti-inflammatory and very low toxicity, thus meeting an important requirement for pharmacological applications. The 3-hydroxylation with morin increases compared with the unsubstituted flavones in 3-position the antioxidative properties thereof. Due to its low pKa value of 3.5 (3-OH-group) morin is present under physiological conditions in deprotonated form and hardly adsorbs, unlike other flavonoids, to negatively charged DNA or RNA. Morin (1) complexes as excellent anionic ligand transition metal cations (e.g. 2:1-complex with $Zn^{2+}$) and lanthanoid cations (e.g. 3:1-complex with Lai under deprotonation of the 2'-OH— or 3-OH-group and is used in the fluorometric chemical analysis of various metal ions. With $Al^{3+}$ a green fluorescent 3:1 complex.

I

To this day, morin is isolated for commercial use from the extract of the yellow wood. However, commercially available morin (obtained naturally as well as synthetically) shows a purity of approx. only 85% with mostly the secondary component kaempferol (II) as impurity, which is missing—compared to morin—the 2'-hydroxy group. Furthermore, there are further impurities, which are usually a mixture of polyphenols/flavonoids. Said impurities, which can be removed only with extreme effort or not at all, interfere with many applications, such as pharmaceuticals as well as electroplating or galvanisation.

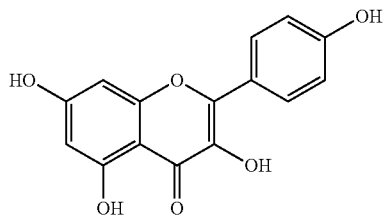

(II)

Therefore, there is a need to provide a method for the direct synthetic production of high-purity morin and morin derivatives. Plus, yellow wood is a tropical wood, which makes using it questionable for environmental reasons.

On the laboratory scale, two synthetic paths are described in the prior art. Although the structure of morin was already explained by Perkin in 1896, and comprehensive literature about the synthesis of flavonoids already exists in general, morin was not synthesised until 2013, wherein an Allan-Robinson condensation based on 2-methoxy-1-(2,4,6-trihydroxyphenyl)ethan-1-one and 2,4-dimethoxybenzoylchloride is used (CN 103342690 A). Furthermore, a similar route to morin was described, which uses chalcone (E)-3-(2,4-Dimethoxyphenyl)-1-(2-hydroxy-4,6-dimethoxyphenyl) prop-2-en-1-one (8) (CN 105985306). Utilised here is the aldol condensation of the acetophenone derivative 1-(2-Hydroxy-4,6-dimethoxyphenyl)ethane-1-one with 2,4-dimethoxybenzaldehyde. Described at last is a synthesis path that is supposed to work without the methylation of the phenolic hydroxy groups (B. Vyas, M. Singh, M. Kaur, O. Silakari, M. S. Bahia, B. Singh, *Med. Chem. Res.* 2016, 25, 609-626).

The aim of the present invention is to provide a method for producing high-purity morin and morin derivatives, which is based on readily available and inexpensive raw materials, as well as providing high-purity synthetically produced morin and morin derivatives, i.e. without the abovementioned impurities. The term morin derivative is understood in the present case as to comprising derivatives directly producible from morin as well as compounds having at least the carbon skeleton of morin, including oxygenation sample, of high purity.

Said aim is achieved by a method for producing a compound with the following formula (1),

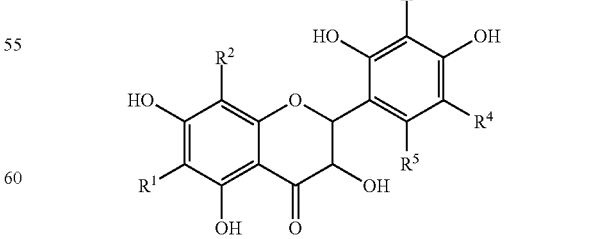

(1)

comprising the steps:

i) Acetylation of a compound with the following formula (4)

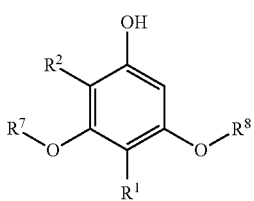

(4)

for forming the acetophenone of the formula (6),

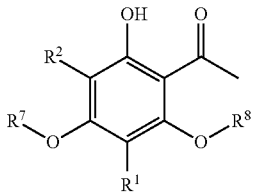

(6)

ii) Transforming the acetophenone of formula (6) with a compound of the following formula (7) under alkaline conditions at room temperature

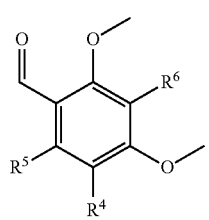

(7)

for forming the chalcone of the following formula (8)

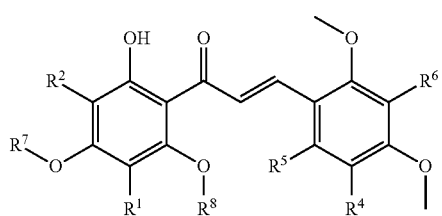

(8)

iii) Transforming the chalcone of formula (8) under oxidising conditions in an alkaline environment for forming a flavonol with the following formula (9); and

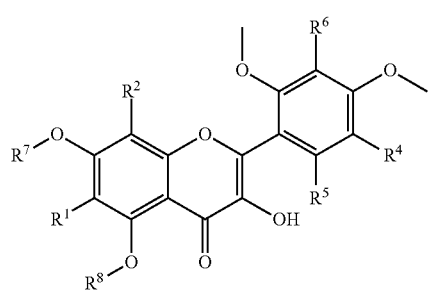

(9)

iv) Demethylation of the flavonol of formula (9), wherein $R^1$, $R^2$, $R^3$, $R^4$, $R^6$ and $R^8$ are independently of one another a branched or C1-C8-Alkyl, $NO_2$, $SO_3H$, $NX_2$, wherein X is an ethyl residue or methyl residue, are CF3 or hydrogen, preferably C1-C5-Alkyl or hydrogen, most preferably C1-C3-Alkyl or hydrogen, and $R^7$ and $R^8$ are independently of one another a methyl-, ethyl-, tert- butyl-, benzyl-, methoxymethyl-, p-methoxybenzyl-, benzyloxymethyl-, triphenylmethyl-, tetrahydropyranyl- or allyl group.

Here, the method is based on readily available raw materials and offers high yield for the desired product. Plus, the product is obtained in high purity, thus showing a higher activity than naturally obtained morin.

Additionally or alternatively, the method can comprise a step (i-a) Methylation of a compound of the following formula (3)

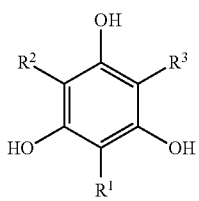

(3)

under acidic conditions for forming a compound of formula (4), wherein $R^1$, $R^2$, $R^3$, $R^4$, $R^5$ and $R^6$ are defined as above.

This allows to synthesise morin or morin derivatives from further, readily available raw materials, e.g. the commercially available trimethoxybenzene, which can be used directly.

In a preferred embodiment $R^3$ is hydrogen. In a particularly preferred embodiment $R^1$, $R^2$, $R^3$, $R^4$, $R^5$ and R are hydrogen. Thus, obtained by the method according to the invention is a particularly preferred high-purity morin of formula I:

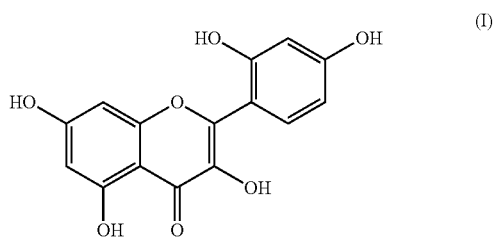 [SMILES: O=c1c(O)c(-c2ccc(O)cc2O)oc2cc(O)cc(O)c12]

(I)

In step iii), the oxidising conditions can be produced preferably by means of tert.-butylhydroperoxide and the alkaline environment by means of an alkali hydroxide. Here, alkali hydroxides are LiOH, KOH and NaOH. Using tertabutylhydroperoxide decreases the formation of unwanted by-products with aurone skeleton and also increases the yield.

In step ii), the alkaline conditions can be produced by means of an alkali hydroxide. Additionally, the reaction can take place at room temperature.

In step i), the acetylation can take place by means of acetyl chloride in the presence of a Lewis acid and dichloromethane. Here, Lewis acids can be preferably boron trichloride, BBr$_3$ or AlCl$_3$ or mixtures thereof, AlCl$_3$ or boron trichloride is particularly preferred.

In step (i-a), the acidic conditions can be produced by means of an inorganic acid. Here, inorganic acids are preferably nitric acid, hydrochloric acid or sulfuric acid.

Furthermore, the aim is achieved by providing a kaempferol-free compound with the formula (1), obtainable through the method according to the invention. In a particularly preferred embodiment, in the compound of the formula (1) R$^1$, R$^2$, R$^3$, R$^4$, R$^5$ and R$^6$ are hydrogen, i.e. the compound is kaempferol-free morin of the formula (I). The morin according to the invention stands out due to very high purity; preferably the purity is more than 85%, 90% or very particularly preferably more than 95%, in particularly preferred embodiments a purity of 99% is achieved. In the present case, purity means that polyphenols/flavonoids are detectable only in the abovementioned quantity. In particular, according to the invention the morin is, as already mentioned, free of kaempferol impurities, i.e. free of kaempferol of the formula (II) and/or its derivates. In the present case the term "free of" means that within the scope of the usual measuring accuracy kaempferol or the derivates thereof are present in a percentage of less than 0.5%, in specific embodiments of less than 0.3%. In particularly preferred embodiments kaempferol or its derivates are not detectable within the scope of measuring accuracy. The high-purity morin available according to the invention can be used, for instance, directly without further filtration in the electrolytic deposition of tin or tin/lead (e.g. according to EP 810303 A1 or DE 19623274 A1). It was found that the activity of the morin in the Sn and SN/PB deposition does not correlate in a linear manner with the content of morin in the natural product used so far, which can be attributed to non-removable impurities, particularly kaempferol and polyphenols and flavonoids. One assumes that natural impurities that so far cannot be removed technically lower the activity of the morin. The pure synthesis product according to the present invention does not contain said natural impurities and therefore shows an activity improved by 22.35% compared with the natural product. Improved activity as defined by the present invention here means covering a sheet metal enlarged by said percentage with Sn or Sn/Pb in a galvanically so-called Hull cell as described in detail in EP 810303 A1. Furthermore, the porosity of the tin or tin/lead layer obtained by means of the morin according to the invention (measured by means of moisture transport FSP, Diss. H. Künzel, Univ. Stuttgart 1994) is lower by approx. 35% than in the comparative example that was usually produced with the natural morin. It was determined here that the improved properties are always in the same range (within the scope of the usual measuring tolerances) irrespective of the source of supply of the natural morin tested in the present case (Sigma-Aldrich, Adooq Bioscience, Aurantika, Fisher-Scientific).

Below, the invention is explained by means of examples that, however, should not be understood as limiting.

EXAMPLE 1

Producing 3,5-dimethoxyphenol (4)

Under an argon atmosphere, phloroglucinol (3) (80.0 g, 634 mmol, 1.0 eq.) was solubilised in methanol (400 mL). Slowly, sulfuric acid (95%, 46.3 mL, 825 mmol, 1.3 equivalent) was added dropwise, and the reaction mixture was stirred for 26 hrs at 80° C. under reflux. Subsequently, 10% aqueous potassium carbonate solution (800 mL) and toluol (300 mL) were added. After separating the phases, the aqueous solution was extracted twice with toluol (300 ml, respectively). The aqueous phase was brought with 2 M HCl solution to pH<2 and extracted three times with ethyl acetate (je 300 ml, respectively). The combined organic phases were dried over sodium sulphate, and the solvent removed in high vacuum. After purification by means of fractional distillation compound (4) (81.2 g, 527 mmol, 83%) was obtained as colourless oil. Additionally, it was possible to obtain by-product (5) (4.71 g, 28.0 mmol, 4.4%) as colourless oil, 3,5-Dimethoxyphenol (4): Boiling point: 139-141° C. (2.8 mbar). DC [Petrol ether/Ethyl acetate (2:1)]: R$_f$=0.40. (400 MHz, CDCl$_3$): δ=6.08 (t, J=2.2 Hz, 1H, 4-CH), 6.03 (d, J=2.2 Hz, 2H, 2-CH, 6-CH), 5.19 (s, 1H, OH), 3.75 (s, 6H, OCH$_3$). $^{13}$C-NMR (100 MHz, CDCl$_3$): d=162.0 (2C, C$_{Ph}$—OCH$_3$), 157.7 (C$_{Ph}$—OH), 94.6 (2C, C-2, C-6), 93.5 (C-4), 55.7 (2C, OCH$_3$). IR (Diamant-ATR): $\tilde{V}$=3384 (m, br.), 3003 (w), 2942 (w), 2842 (w), 1595 (s), 1500 (m), 1458 (m), 1433 (m), 1342 (m), 1294 (m), 1 192 (s), 1 139 (s), 1052 (s), 992 (m), 973 (m), 924 (m), 818 (a), 679 (m). UV (MeOH): λ$_{max}$ (lg ε)=267 (2.79), 206 (4.60). MS (EI): m/z (%)=69 [M-MeOC—CH—COH]$^+$ (18), 125 [M-COH]$^+$ (60), 154 [M]$^+$ (100).

It was possible to obtain the product in a yield of 78%. This was mainly possible due to the second extraction of the aqueous phase after reducing the pH value, which results in an additional 23% yield of the product. Increasing the reaction time was necessary especially in larger batches; it was increased from 21 hrs at 500 mg batches to 30 hrs at 20 g batches. The characterisation analyses of the product met the expectations.

During the reaction, two by-products were fond and isolated. One of them is the single-methylated 5-Methoxy-benzol-1,3-diol, which was possible to be confirmed by $^1$H-NMR and $^{13}$C-NMR analyses. The yield was here at 15%. The other by-product is the thrice-methylated 3,5-Trimethoxybenzol, which occurred at a yield of 7%. $^1$H-NMR and $^{15}$C-NMR analyses were also able to confirm the structure. By-product 1,3,5-Trimethoxybenzol (5) [12]: yield: 7©, DC [Petrol ether/Ethyl acetate (2:1)]: R$_f$=0.78. Boiling point: 135-137° C. (2.8 mbar). $^1$H-NMR (400 MHz, CDCl$_3$): d=6.09 (s, 3H, Ph-H), 3.77 (s, 9H, OCH$_3$). $^{13}$C-NMR (100 MHz, CDCl$_3$): d=161.6 (3C, C$_{Ph}$—OCH$_3$), 92.9 (3C, Cp$_h$), 55.3 (3C, OCH$_3$). IR (Diamant-ATR): $\tilde{V}$=3075 (w), 3004 (m), 2963 (m), 2940 (m), 2839 (m), 1591 (s), 1480 (m), 1456 (s) 1423 (m), 1339(m), 1322 (m), 1252 (w), 1209 (a), 1 194 (m), 1 147 (a), 1064 (s), 1034 (a), 990 (m), 942 (m), 916 (m), 847 (s), 822 (s), 779 (s), 686 (s), 640 (m), 616 (m), 591 (m), 537 (m). UV (MeOH): λ$_{max}$ (lg ε) 266 (2.62), 207 (4.47). MS (EI): m/z (%)=69 [M-MeOC—CH—COMe]$^+$ (83), 125 [M-COMe]$^+$ (100), 167 [M]$^+$ (100).

Example 2

Producing 1-(2-Hydroxy-4,6-dimethoxyphenyl)ethane-1-one (6)

Under an argon atmosphere, boron trichloride (1 M in dichloromethane, 48.9 mL, 48.9 mmol, 1.0 eq.) was solubilised in dichloromethane (50 ml) and cooled to −10° C. 3,5-Dimethoxyphenol (4) (7.54 g, 48.9 mmol, 1.0 eq.), pre-solubilised in dichloromethane (25 mL), was added dropwise. The reaction mixture was brought to room temperature and stirred for 30 min. Subsequently, acetyl chloride (4.54 ml, 63.6 mmol, 1.3 eq.), pre-solubilised in dichloromethane (80 ml), was added dropwise within 15 min. The reaction mixture was stirred for 3 hrs under reflux. After cooling, the 1 M aqueous HCl solution (300 ml) was added. The phases were separated, and the aqueous phase extracted three times with ethyl acetate (200 ml, respectively). The combined organic phases were dried over sodium sulphate, and the solvent removed in high vacuum. After column-chromatographic cleaning on silica gel [Petrol ether/Ethyl acetate (2:1)] the acetophenone derivative (6) (7.38 g, 37.6 mmol, 77%) was obtained as colourless solid. DC [Petrol ether/Ethyl acetate (2:1)]: 0.73. Melting point: 79-82° C. $^1$H-NMR (400 MHz, DMSO-$d_6$): δ=14.03 (s, 1H, OH), 6.06 (d, J=2.4 Hz, 1H, 5-CH), 5.92 (d, J=2.4 Hz, 1H, 3-CH), 3.85 (s, 3H, o-Ph-OCH$_3$), 3.82 (s, 3H, p-Ph-OCH$_3$), 2.61 (s, 3H, O=CCH$_3$). $^{13}$C-NMR (100 MHz, DMSO-$d_6$): δ=203.2 (C=0), 167.6 (p-$C_{Ph}$—OCH$_3$), 166.1 (o-$C_{Ph}$—OCH$_3$), 162.9 (o-$C_{Ph}$—OH), 106.0 ($C_{Ph}$—C=0), 93.5 (C-5), 90.75 (C-3), 55.5 (2C, OCH$_3$), 32.9 (CH$_3$). IR (Diamant-ATR): v=3103 (w, br.), 3008 (w), 2945 (w, br.), 2849 (w, br.), 2705 (w, br.), 2599 (w, br.), 1613 (s), 1457 (m), 1441 (m), 1423 (m), 1389 (m), 1366 (m), 1325 (m), 1269 (s), 1220 (s), 1205 (s), 1 155 (s), 11 12 (m), 1081 (m), 1045 (m), 1030 (m), 962 (m), 941 (m), 893 (m), 835 (s), 806 (m), 744 (m), 715 (w), 690 (w), 657 (m), 628 (w), 596 (m), 557 (m), 531 (m). UV (MeOH): $λ_{max}$ (lg ε)=286(4.26), 209 (4.21). MS (ESI): m/z (%)=197 [M+H]$^+$ (49), 219 [M+Na]$^+$ (100). HRMS (ESH+): m/z=219.06279 (0.1 ppm, ber.: 219.06278 [M+Na]$^+$).

Example 3

Producing 3-(2,4-Dimethoxyphenyl)-1-(2-hydroxy-4,6-dimethoxyphenyl)prop-2-en-1-one (8)

Under an argon atmosphere, the acetophenone derivative (6) (4.80 g, 24.5 mmol, 1.0 eq.) and 2,4-Dimethoxybenzaldehyde (7) (6.01 g, 36.7 mmol, 1.5 eq.) were solubilised in ethanol (150 ml). A solution of NaOH (8.80 g, 220 mmol, 9.0 eq.) in distilled water (38 ml) was added dropwise. The reaction mixture was stirred for 17 hrs at room temperature. Subsequently, 1 M aqueous HCl solution (350 ml) was added and stirred for another 15 min. The solution was extracted three times with ethyl acetate (250 ml, respectively). The combined organic phases were dried over sodium sulphate, and the solvent removed in high vacuum. After column-chromatographic cleaning on silica gel [Petrol ether/Ethyl acetate (3: 1-1:1)] the chalcone (8) (5.87 g, 17.0 mmol, 70%) was obtained as yellow solid. DC [Petrol ether/Ethyl acetate (4:1)]: $R_f$=0.32. Melting point.: 126-129° C. $^1$H-NMR (400 MHz, CDCl$_3$): d=14.54 (s, 1H, 2'-OH), 8.10 (d, J=15.7 Hz, 1H, ß-H), 7.90 (d, J=15.7 Hz, 1H, a-H), 7.54 (d, J=8.6 Hz, 1H, 6-H), 6.53 (dd, J=8.6, 2.4 Hz, 1H, 5-H), 6.47 (d, J=2.4 Hz, 1H, 3-H), 6.10 (d, J=2.4 Hz, 1H, 3'-H), 5.95 (d, J=2.4 Hz, 1H, 5'-H), 3.90 (s, 3H, 6'-OCH$_3$), 3.89 (s, 3H, 2-OCH$_3$), 3.85 (s, 3H, 4-OCH$_3$), 3.83 (s, 3H, 4'-OCH$_3$). $^{13}$C-NMR (100 MHz, CDCl$_3$): d=193.0 (C=0), 168.3 (C-6'), 165.8 (C-4'), 162.8 (C-4), 162.4 (C-2'), 160.2 (C-2), 138.3 (C-ß), 130.4 (C-6), 125.3 (C-a), 1 17.8 (C-1), 106.5 (C-1'), 105.5 (C-5), 98.4 (C-3), 93.8 (C-5'), 91.1 (C-3'), 55.7 (2'-OCH$_3$), 55.5 (2-OCH$_3$), 55.5 (4'-OCH$_3$), 55.4 (4-OCH$_3$), IR (Diamant-ATR): $\tilde{V}$=3120 (w, br.), 3082 (w, br.), 3000 (w), 2942 (m, br.), 2840 (w, br.), 1604 (s), 1547 (s), 1502 (s), 1451 (m), 1437 (m), 1414 (m), 1343 (m), 1315 (m), 1293 (m), 1268 (s), 1206 (s), 1158 (s), 1 106 (s), 1057(m), 1028 (s), 980 (m), 940 (m), 867 (m), 849 (m), 814 (s), 795 (s), 767 (m), 720 (m), 697 (m), 674 (m), 648 (m), 621 (m), 604 (m), 582 (m), 563 (m), UV (MeOH): $λ_{max}$ (lg ε)=379 (4.52), 251 (3.95), 207 (4.60). MS (EI): m/z (%)=345 [M+H]$^+$ (47), 367 [M+Na]$^+$ (67), 71 1 [2M+Na]$^+$ (100). HRMS (ESI+): m/z=71 1.24176 (0.1 ppm, ber.: 71 1.24120 [2M+Na]$^+$).

Example 4

Producing 2-(2,4-Dimethoxyphenyl)-3-hydroxy-5,7-dimethoxy-4//-chromen-4-one (9)

Under an argon atmosphere, the chalcone (8) (1.00 g, 2.90 mmol, 1.0 eq.) was solubilised in ethanol (40 ml). A solution of tert-Butylhydroperoxide (70% in H2O, 4.0 ml, 29.0 mmol, 10 eq.) and NaOH (1.74 g, 43.6 mmol, 15 eq.) in distilled H2O 2O (4 ml) was added and stirred for 23 hrs at room temperature. Subsequently, aqueous HCl solution (1.0 M, 100 ml) was added and extracted three times with ethyl acetate (80 ml, respectively). The combined organic phases were dried over sodium sulphate, and the solvent removed in high vacuum. After column-chromatographic cleaning on silica gel [Petrol ether/Ethyl acetate (1:4)] the flavonol (9) (395 mg, 1.10 mmol, 38%) was obtained as yellow solid, in addition to the aurone (10) (44 mg, 0.13 μmol, 4.5%). Likewise, the hydroxylated aurone derivative (11) was obtained (118 mg, 329 μmol, 11%). DC [Petrol ether/Ethyl acetate (1:4)]: $R_f$=0.45. Melting point: 1 10-1 12° C. $^1$H-NMR (600 MHz, CDCl$_3$): d=7.50(d, J=8.4 Hz, 1H, 6'-CH), 6.78 (s, 1H, OH), 6.61 (dd, J=8.4, 2.4 Hz, 1H, 5'-CH), 6.58 (d, J=2.3 Hz, 1H, 3'-CH), 6.48 (d, J=2.3 Hz, 1H, 8-CH), 6.34 (d, J=2.3 Hz, 1H, 6-CH), 3.97 (s, 3H, 4'-OCH$_3$), 3.87 (s, 6H, 2'-OCH3, 7-OCH$_3$), 3.84 (s, 3H, 5-OCH)). $^{13}$C-NMR (150 MHz, CDCl$_3$): d=172.0 (C-4), 164.1 (C-7), 162.7 (C-4'), 160.6 (C-5), 159.6 (8C—C-10), 158.8 (C-2'), 142.7 (C-2), 138.6 (C-3), 131.9 (C-6'), 1 12.4 (C-1), 106.8 (4C—C-5C), 104.8 (C-5'), 99.2 (C-3'), 95.6 (C-6), 92.6 (C-8), 56.4 (4'-OCH$_3$), 55.9 (5-OCH$_3$), 55.8 (2'-OCH$_3$), 55.5 (7-OCH$_3$). IR (Diamant-ATR): $\tilde{V}$=3204 (m, br.), 3006 (w), 2961 (m), 2938 (m), 2840 (w), 1728 (m), 1658 (m), 1601 (s), 1499 (m), 1461 (m), 1435 (m), 1414 (m), 1373 (m), 1317 (m), 1299 (m), 1281 (m), 1252 (m), 1206 (s), 1 161 (s), 1 120 (m), 1092 (m), 1024 (m), 1002 (m), 967 (m), 936 (m), 918 (m), 873 (m), 814 (m), 742 (w), 677 (w), 639 (m), 599 (m), 552 (m). UV (MeOH): $λ_{max}$ (lg ε)=338 (4.07), 286 (3.89), 246 (4.32), 203 (4.64). MS (ESI): m/z (%)=359 [M+H]$^+$ (40), 381 [M+Na]$^+$ (56), 739 [2M+Na]$^+$ (100). HRMS (ESI+): m/z=739.20013 (0.02 ppm, ber.: 739.20028 [2M+Na]$^+$).

By-product 2-(2,4-Dimethoxybenzyliden)-4,6-dimethoxybenzofuran-3(2/-/)-one (10): DC [Petrol ether/Ethyl acetate (1:4)]: =0.44. $^1$H-NMR (400 MHz, CDCl$_3$): δ=8.19 (d, J=8.7 Hz, 1H, 6'-H), 7.27 (s, 1H, 2C=CH), 6.58 (dd, J=8.7, 2.4 Hz, 1H, 5'-H), 6.45 (d, J=2.4 Hz, 1H, 3'-H), 6.36 (d, =1.9 Hz, 1H, 7H), 6.1 1 (d, J=1.9 Hz, 1H, 5H), 3.94 (s, 3H, 4-OCH$_3$), 3.90 (s, 3H, 6-OCH$_3$), 3.87 (s, 3H, 2'-OCH$_3$), 3.86 (s, 3H, 4'OCH$_3$). $^{13}$C-NMR (100 MHz, CDCl$_3$): d=180.6 (C-3), 168.6 (7-C—C-10), 168.4 (C-6), 162.2 (C-4'), 160.1 (C-2'), 159.3 (C-4), 146.8 (C-2), 132.8 (C-6'), 1 14.7 (C-1'), 105.7 (3C—C-4C), 105.5 (C-5'), 105.3 (2C=C), 98.0 (C-3'), 93.8 (C-5), 89.1 (C-7), 56.2 (4-OCH$_3$), 56.0 (6-OCH$_3$), 55.6 (2'—OCH$_3$), 55.4 (4'-OCH$_3$). IR (Diamant-ATR): $\tilde{V}$=2975 (w, br.), 2945 (w, br.), 2836 (w, br.), 1689 (m), 1648 (m), 1590 (s, br.), 1503 (m), 1447 (m), 1419 (m), 1362 (m), 1350 (m), 1321 (m), 1289 (m), 1243 (s), 1217 (s), 1201 (s), 1 155 (s), 1087 (s), 1033 (s), 946 (m), 917 (m), 890 (m), 815 (s), 788 (s), 720 (m), 695 (m), 674 (m), 633 (m), 589 (m), 548 (m). UV (MeOH): $λ_{max}$ (lg ε)=403 (4.43), 252(3.93), 203 (4.53). MS (ESI): m/z (%)=343 [M+U]⁺ (61), 365 [M+Na]⁺ (100), 707 [2M+Na]⁺ (97). HRMS (ESI+): m/z=365.09975 (0.5 ppm, ber.: 365.09956 [M+Na]⁺).

By-product (E)-2-((2,4-Dimethoxyphenyl)(hydroxy)methylen)-4,6-di methoxybenzofuran-3(2H)-one (11): DC [Petrol ether/Ethyl acetate (1:4)]: R$_f$=0.63. Melting point: 177-180° C. ¹H-NMR (400 MHz, CDCl₃): d=9.47 (s, OH), 7.19 (d, J=7.3 Hz, 6'-H), 6.57 (dd, J=7.3, 2.1 Hz, 5'-H), 6.56 (d, J=2.1 Hz, 3'-H), 6.53 (d, J=2.3 Hz, 7-H), 6.36 (d, J=2.3 Hz, 4-H), 3.99 (s, 3H, 3-COCH₃), 3.86 (s, 3H, 5-COCH₃), 3.83 (S, 3H, 4'-COCH₃), 3.79 (s, 3H, 2'-COCH₃). ¹³C-NMR (100 MHz, CDCl₃): d=170.72 (3-C), 162.87 (6-C), 161.80 (2-C), 160.85 (4'-C), 158.67 (2'-C), 157.01 (4-C), 155.80 (7-C—C-1-0), 132.46 (6'-C), 112.98 (C—OH), 104.70 (5'-C), 100.41 (1'-C), 99.15 (3'-C), 99.09 (3-C—C-4-C), 95.37 (5-C), 94.26 (7-C), 56.86 (4-C—CH₃), 55.86 (6-C—CH₃), 55.77 (2'-C—CH₃), 55.68 (4'-C—CH₃). IR (Diamant-ATR): $\tilde{V}$=3319 (m, br.), 3211 (w, 3004 (m), 2951 (m, br.), 2841 (m), 2678 (w, br.), 1703(m), 1603 (s), 1576 (s), 1510 (m), 1446 (m), 1368 (m), 1281 (m), 1256 (m), 1204 (5), 1155 (s), 1 110 (5), 1027 (a), 935 (m), 817 (m), 750 (m), 686 (m), 636 (m), 617 (m). UV (MeOH): λ$_{max}$ (lg ε)=621 (1.71), 314 (3.71), 295 (3.72), 253 (3.86), 206 (4.39), 203 (4.39). MS (ESI): m/z (%)=381 [M+Na]⁺ (100), 739 [2M+Na]⁺ (42), HRMS (ESI+): m/z=381.09460 (1.10 ppm, ber.: 381.09502 [M+Na]⁺).

Example 5

Producing 2-(2,4-Dihydroxyphenyl)-3,5,7-trihydroxy-4H-chromen-4-one (1, Morin)

Under an argon atmosphere, the flavonol (9) (400 mg, 1.12 mmol, 1.0 eq.) was solubilised in acetic acid (99%, 10 ml) and HBr (48% in H₂O, 50 ml) added. Subsequently, heating took place for 24 hrs under reflux. The solvent was removed from the raw material as much as possible and received in ethanol (2 ml). After adding petrol ether (100 ml), filtration and drying of the residue on the high vacuum, morin ((1), 220 mg, 728 μmol, 65%) was obtained as deep-red solid. RP-DC [Water/Methanol (1:1)]: Ri=0.35. Melting point: >250° C. ¹H-NMR (400 MHz, DMSO-d₆): δ=12.64 (a, 5-C—OH, 1H), 10.72 (s, COH, 1H), 9.79 (s, 4'-COH, 1H), 9.35 (s, COH, 1H), 8.89 (s, COH, 1H), 7.24 (d, J=8.4 Hz, 6'-CH, 1H), 6.41 (d, J=2.1 Hz, 3'-CH, 1H), 6.36 (dd, J=8.5, 2.3 Hz, 5'-CH, 1H), 6.30 (d, J=2.1 Hz, 8-CH, 1H), 6.18 (d, J=2.0 Hz, 6-CH, 1H). ¹³C-NMR (100 MHz, DMSO-d₆): d=176.2 (C-4), 163.7 (C-7), 160.9 (C-5), 160.4 (C-4'), 156.8 (2C, C-2', C-8a), 149.0 (C-2), 136.2 (C-3), 131.7 (C-6'), 109.3 (C-1'), 106.8 (C-5'), 103.6 (C-4a), 103.0 (C-2'), 98.0 (C-6), 93.4 (C-8). IR (Diamant-ATR): $\tilde{V}$=3212 (m, br.), 2731 (m, br.), 2341 (m, br.), 2116 (w, br.), 1995 (w, br.), 1920 (w, br.), 1655 (m), 1626 (m), 1594 (m), 1570 (m), 1515 (m), 1480 (m), 1412 (m), 1365 (m), 1311 (m), 1263 (m), 1224 (m), 1167 (s), 1102 (m), 1080 (m), 1011 (m), 983 (m), 969 (m), 874 (m), 833 (m), 805(m), 793 (m), 730 (m), 703 (m), 689 (m), 651 (m), 635 (m), 618 (m), 579 (m), 566 (m), 543 (m). UV (MeOH): λ$_{max}$ (lg ε)=372 (4.12), 263 (4.25), 205 (4.59). MS (ESI): m/z (%)=301 [M–H]– (100), 303 [M+H]+(24), 325 [M+Na]⁺ (100), 627 [2M+Na]⁺ (23), 739 [2M+Na]⁺ (100). HRMS (ESI+): m/z=325.03212 (0.92 ppm,bPer.: 325.03242 [M+Na]⁺.

The invention claimed is:
1. A method for producing a compound of formula (1)

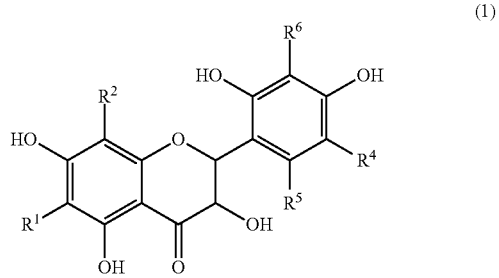

comprising the following steps:
i) acetylation of a compound of formula (4)

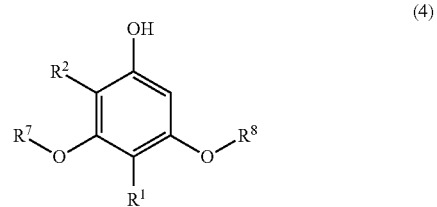

to form an acetophenone of formula (6)

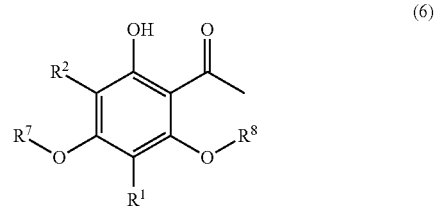

ii) transforming the acetophenone of formula (6) with a compound of formula (7) under alkaline conditions

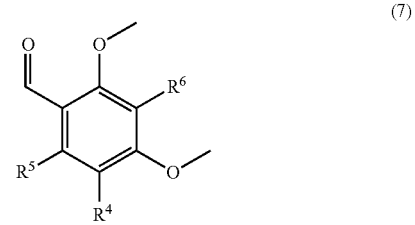

at room temperature to form a chalcone of formula (8)

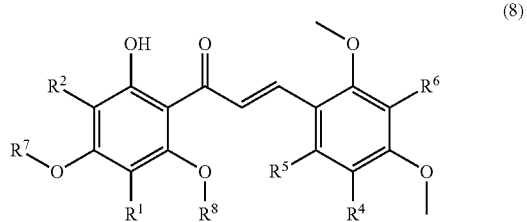

iii) transforming the chalcone of formula (8) under oxidising conditions in an alkaline environment to form a flavonol of formula (9)

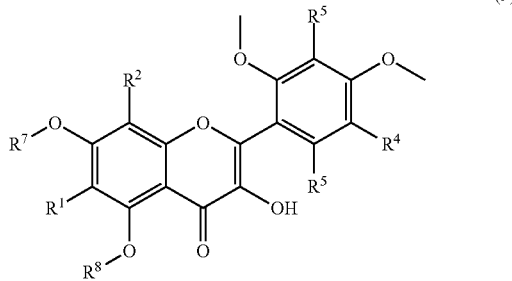

(9)

iv) and demethylation of the flavonol of formula (9), wherein $R^1$, $R^2$, $R^4$, $R^5$ and $R^8$ are a branched or linear $C_1$-$C_8$-alkyl, $NO_2$, $SO_3H$, $NX_2$, wherein X is ethyl gr methyl, $CF_3$ or hydrogen, and $R^7$ and $R^8$ are independently of one another a methyl-, ethyl-, t-butyl-, benzyl-, methoxymethyl-, p-methoxybenzyl-, benzyloxymethyl-, triphenylmethyl-, tetrahydropyranyl- or allyl group.

2. The method according to claim 1, wherein $R^1$, $R^2$, $R^4$, $R^5$ and $R^6$ are $C_1$-$C_5$-alkyl or hydrogen.

3. The method according to claim 1, wherein $R^1$, $R^2$, $R^4$, $R^5$ and $R^6$ are $C_1$-$C_3$-alkyl or hydrogen.

4. The method according to claim 1, further comprising step (i-a):

(i-a) methylation of a compound of formula (3)

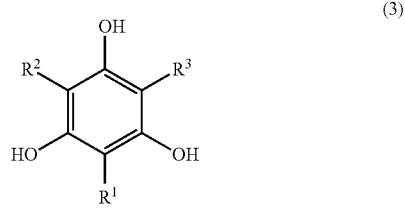

(3)

under acidic conditions to form the compound of formula (4), wherein $R^1$, $R^2$, $R^4$, $R^5$ and $R^6$ are defined as in claim 1, and wherein $R^3$ is a branched or linear $C_1$-$C_8$-alkyl, $NO_2$, $SO_3H$, $NX_2$, wherein X is ethyl or methyl, $CF_3$ or hydrogen.

5. The method according to claim 4, wherein $R^3$ is hydrogen.

6. The method according to claim 1, wherein $R^1$, $R^2$, $R^4$, $R^5$ and $R^6$ are hydrogen.

7. The method according to claim 1, wherein, in step iii), the oxidising conditions are produced by means of tert-butylhydroperoxide and the alkaline environment is produced by means of an alkali hydroxide.

8. The method according to claim 1, wherein, in step ii), the alkaline conditions are produced by means of an alkali hydroxide and the reaction takes place at room temperature.

9. The method according to claim 1, wherein, in step i), the acetylation takes place by means of acetyl chloride in the presence of a Lewis acid and dichloromethane.

10. The method according to claim 1, wherein in, step (i-a), the acidic conditions are produced by means of an inorganic acid.

11. A method for the electrolytic deposition of tin or tin/lead on a metal sheet, such method comprising the addition of one or more compounds of formula (1)

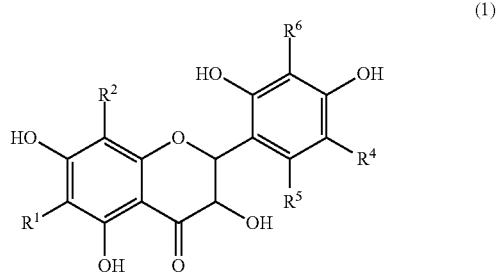

(1)

wherein $R^1$, $R^2$, $R^4$, $R^5$ and $R^6$ are a branched or linear $C_1$-$C_8$-alkyl, $NO_2$, $SO_3$, $NX_2$, wherein X is ethyl or methyl, $CF_3$ or hydrogen, to an electroplating bath comprising a tin or tin/lead electroplating solution and applying a current to the metal sheet, wherein the addition of the one or more compounds of formula (1) to the electroplating solution results in a tin or tin/lead layer obtained exhibiting 20% lower tin or tin/lead layer porosity when compared to such method wherein the one or more compounds of formula (1) were not added to the electroplating solution.

12. The method according to claim 11, wherein the tin or tin/lead layer obtained exhibits 35% lower tin or tin/lead layer porosity.

13. The method according to claim 11, wherein $R^1$, $R^2$, $R^4$, $R^5$ and $R^6$ are $C_1$-$C_5$-alkyl or hydrogen.

14. The method according to claim 11, wherein $R^1$, $R^2$, $R^4$, $R^5$ and $R^6$ are $C_1$-$C_3$-alkyl or hydrogen.

* * * * *

UNITED STATES PATENT AND TRADEMARK OFFICE
CERTIFICATE OF CORRECTION

PATENT NO. : 11,312,696 B2
APPLICATION NO. : 16/765594
DATED : April 26, 2022
INVENTOR(S) : Thomas Lindel and Steffen Mende Page 1 of 2

It is certified that error appears in the above-identified patent and that said Letters Patent is hereby corrected as shown below:

In the Specification

Column 2, Lines 50 to 65, formula (1) should read:

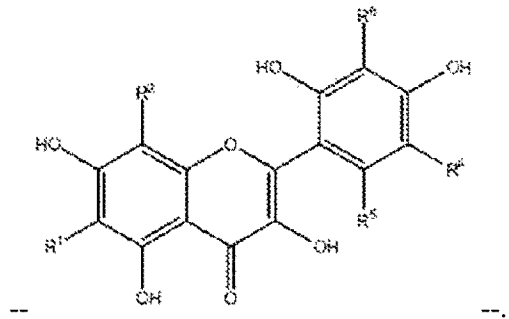
-- --.

In the Claims

Claim 1, Column 10, formula (1) should read:

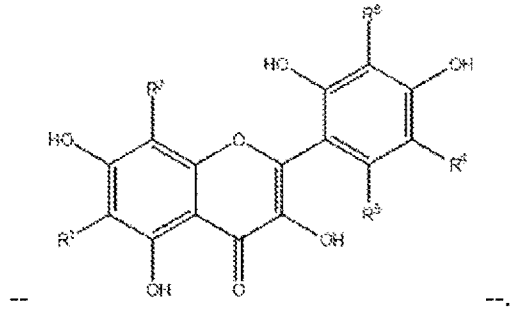
-- --.

Claim 1, Column 11, Line 21: "$R^8$" should read --$R^6$--.
Line 23: "gr" should read --or--.

Signed and Sealed this
Twenty-first Day of June, 2022

*Katherine Kelly Vidal*

Katherine Kelly Vidal
*Director of the United States Patent and Trademark Office*

CERTIFICATE OF CORRECTION (continued)
U.S. Pat. No. 11,312,696 B2

Claim 11, Column 12, formula (1) should read:

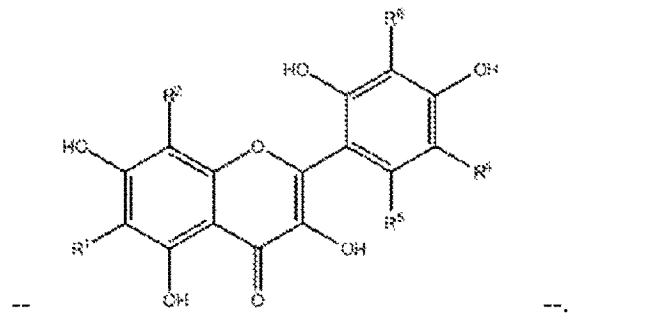

-- --.

Line 35: "$SO_3$" should read --$SO_3H$--.